(12) United States Patent
De Vries et al.

(10) Patent No.: US 9,346,730 B2
(45) Date of Patent: May 24, 2016

(54) PROCESS FOR THE PRODUCTION OF FURFURAL AND LEVULINIC ACID FROM LIGNOCELLULOSIC BIOMASS

(71) Applicant: DSM IP Assets B.V., Heerlen (NL)

(72) Inventors: Johannes Gerardus De Vries, Echt (NL); Johannes Augustinus Kroon, Echt (NL); Rudy Francois Maria Jozef Parton, Echt (NL); Pierre Louis Woestenborghs, Echt (NL); Arie De Rijke, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 667 days.

(21) Appl. No.: 13/941,297

(22) Filed: Jul. 12, 2013

(65) Prior Publication Data

US 2014/0018555 A1    Jan. 16, 2014

(30) Foreign Application Priority Data

Jul. 13, 2012  (EP) .................................... 12176284

(51) Int. Cl.
*C07D 307/50*    (2006.01)
*C07C 51/00*    (2006.01)

(52) U.S. Cl.
CPC ..................... *C07C 51/00* (2013.01)

(58) Field of Classification Search
USPC .......................................... 549/489; 562/515
See application file for complete search history.

(56) References Cited

FOREIGN PATENT DOCUMENTS

| WO | 8910362 A1 | 11/1989 |
|---|---|---|
| WO | 9819986 A1 | 5/1998 |

OTHER PUBLICATIONS

Extended European Search Report for EP12176284.3 Dated Nov. 27, 2012.

*Primary Examiner* — Bernard Dentz
(74) *Attorney, Agent, or Firm* — Miles & Stockbridge, P.C.

(57) ABSTRACT

A process for producing furfural and levulinic acid from lignocellulose-comprising biomass is disclosed. The biomass is slurried using water and optionally an acid, subjected to hydrolysis, and then subjected to a solid/liquid separation to yield at least an aqueous fraction comprising C5 and C6 sugars and a solid fraction comprising cellulose and lignin. Furfural is obtained by adding an organic solvent to the aqueous fraction, heating at 120-220° C. for a sufficient time to form furfural, cooling, and separating an organic phase comprising at least part of the furfural from an aqueous phase. Levulinic acid is obtained by suspending the solid fraction in water and optionally an acid, heating the suspension to 140-220° C., and separating an aqueous fraction comprising the levulinic acid from a solid fraction.

10 Claims, No Drawings

PROCESS FOR THE PRODUCTION OF FURFURAL AND LEVULINIC ACID FROM LIGNOCELLULOSIC BIOMASS

CROSS REFERENCE TO RELATED APPLICATIONS

This application claims priority to European Application No. 12176284.3, filed Jul. 13, 2012, the contents of which is incorporated herein by reference in its entirety.

BACKGROUND

1. Field of the Invention

The present invention relates to a process for the production of levulinic acid and furfural from lignocellulosic biomass.

2. Description of Related Art

The needs of the developed world are currently dependent on the utilisation of fossil fuels to produce industrial chemicals and liquid fuels. The majority of modern synthetic products are thus produced from oil. Concerns over high fuel prices, security of energy, global climate change and develop opportunities for rural economic development pushed governments and industries to what is known as first generation technologies for producing biofuels from for example maize. However due to the only marginal improvement of the effect on the climate change and the competition with food, a second generation technology was developed based on the more abundant lignocellulosic feedstocks. Many of the high potential energy crops require less energy for their production as well as less fertilizers, they result in minimal soil erosion, often increase the soil carbon content and require less water.

Lignocellulosic feedstocks are typically composed of 35 to 55% cellulose, 15 to 35% hemicellulose and 15 to 35% lignin. Lignocellulosic feedstocks can be used to produce biofuels, such as ethanol, but it is also possible to produce other chemicals. Most of the chemicals produced in both first and second generation technology are the result of fermentations.

SUMMARY

The invention provides a process for producing furfural and levulinic acid from lignocellulose-comprising biomass, said process comprising:

(a) adding water and optionally an acid to said biomass to form a slurried biomass;

(b) subjecting said slurried biomass to hydrolysis to form a hydrolysate comprising C5 and C6 sugars and further comprising (insoluble) cellulose and lignin;

(c) subjecting said hydrolysate comprising said C5 and C6 sugars and said (insoluble) cellulose and lignin to solid/liquid separation to yield a first aqueous fraction comprising at least part of said C5 and C6 sugars and a first solid fraction comprising at least part of said cellulose and lignin;

(d) optionally concentrating said first aqueous fraction;

(e) adding an organic solvent to the (optionally concentrated) first aqueous fraction to form a biphasic system;

(f) heating said biphasic system to a temperature within the range of 120-220° C. and maintaining said biphasic system at that temperature range for a time sufficient to form furfural;

(g) cooling the biphasic system comprising furfural obtained in step (f);

(h) optionally subjecting the cooled biphasic system obtained in step (g) to solid/liquid separation and recovering the biphasic system;

(i) subjecting the cooled biphasic system obtained in step (g) or the recovered biphasic system obtained in step (h) to a separation step to yield an organic phase comprising at least part of said furfural and an aqueous phase comprising at least part of said C6 sugars and optionally further comprising furfural;

(j) optionally recovering furfural from said organic phase;

(k) optionally using the recovered organic phase obtained in step (j) to extract furfural from the aqueous phase obtained in step (i) by adding said recovered organic phase to said aqueous phase and repeating step (i) and optionally step (j);

(l) adding water and optionally an acid to the first solid fraction obtained in step (c) to form a suspension;

(m) subjecting the suspension obtained in step (l) to a temperature of between 140 and 220° C. to form levulinic acid;

(n) subjecting the suspension comprising levulinic acid obtained in step (m) to solid/liquid separation to yield a second aqueous fraction comprising levulinic acid and a solid fraction; and (o) optionally recovering said levulinic acid from the second aqueous fraction.

DETAILED DESCRIPTION OF A PREFERRED EMBODIMENT

The inventors have surprisingly found that with the process of the invention levulinic acid and furfural can be produced from lignocellulosic biomass in one process with no or little waste. In other words, both C6 and C5 sugars present in the lignocellulosic biomass can be converted efficiently into valuable compounds levulinic acid and furfural, respectively. Solvents and energy are used in an efficient way. The process may therefore allow for very efficient use of the biomass. The process may include a heat integration step. Less reactor fouling may occur, less insoluble char is produced and the yields of levulinic acid and/or furfural may be improved.

In step (a) water is added to the biomass in order to facilitate hydrolysis. Acid may be optionally added. Suitable acids include inorganic acids such hydrochloric acid, sulphuric acid, nitric acid, and phosphoric acid. Preferred are hydrochloric acid or sulphuric acid or mixtures thereof. Some types of biomass contain acids, such as formic acid or acetic acid; when using such types of biomass adding acid may not be required as the natural acid will result in an acidic pH. Suitable biomass may include hemicellulosic biomass and may comprise wood; lumber processing side products such as saw dust, wood chippings and wood shavings; tree bark. Lignocellulosic biomass typically has a fibrous nature and comprises a bran fraction that contains the majority of lignocellulosic (bran) fibers. Hemicellulosic biomass is typically rich in pentoses; it usually also comprises hexoses and lignin.

In step (b) the slurried biomass which is obtained in step (a) is hydrolyzed to form a hydrolysate comprising C5 and C6 sugars and further comprising (insoluble) cellulose and lignin. The C5 sugars, or pentoses, may be arabinose, ribose, ribulose, xylose, xylulose, and lyxose, preferably it is xylose. Combinations of C5 sugars are also possible. The hydrolysis in step (b) may be carried out at a temperature between 120 and 200° C., more preferably between 140 and 180° C. The pH in step (b) is preferably less than 5, more preferably less than 3.5, even more preferably less than 1.

In step (c) the hydrolysate comprising the C5 and C6 sugars and the (insoluble) cellulose and lignin obtained in step (b) are subjected to solid/liquid separation. This yields an aqueous fraction comprising at least part of said C5 and C6 sugars and a first solid fraction comprising at least part of said cellulose and lignin. Suitable solid/liquid separation techniques include filtration and centrifugation, these are well-known in the art.

In step (d), the aqueous fraction obtained in step (c) may optionally be concentrated, preferably by evaporation. Concentration advantageously reduces the volume in all subsequent steps, meaning using less solvent and/or less energy for heating and cooling. Also, all subsequent reactors and pipes etc. may be smaller.

In step (e) an organic solvent is added to the (optionally concentrated) aqueous fraction obtained in step (c). This will result in a biphasic system. Suitable organic solvents include toluene, methylnaphthalene, alcohols, such as methanol, ethanol, propanol, butanol; ketones, such as for example methylbutylketone; ethers, such as for example anisole (methyl phenyl ether), 2,5,8-trioxanonane (diglyme), diethylether, tetrahydrofuran, 2-methyl-tetrahydrofuran, diphenylether, diisopropylether and the dimethylether of di-ethyleneglycol; esters, such as for example ethyl acetate, methyl acetate, dimethyl adipate and butyrolactone; amides, such as for example dimethylacetamide and N-methylpyrrolidone; sulfoxides and sulphones, such as for example dimethylsulphoxide, di-isopropylsulphone, sulfolane (tetrahydrothiophene-2,2-dioxide) 2-methylsulfolane and 2-methyl-4-ethylsulfolane. Other solvents may also advantageously be used such as DCM (dicholoromethane), DCE (dichloroethene), benzene, 2-Heptanone, Butyl acetate, 1,2-Dichloroethane, Methyl isobutyl ketone, Dichloromethane, Ethyl propionate, 2-Pentanone, Diethyl ether, t-Amyl alcohol, Butanol, Cyclohexanone, Ethyl acetate, Pyridine, Tetrahydrofuran, 2-Butanone, Acetone, Dioxane, Acetonitrile, Methanol, N,N-Dimethylformamide, Dimethyl sulfoxide, Formamide, Ethylene glycol, 2-ME-THF (2-methyl tetrahydrofuran), MTBE (methyl-ter-butylether), MiBK (methyl isobutylketone), HOAc (acetic acid), CPMe (cyclopentyl methylether), heptane, DMF (dimethyl formamide), NMP (N-methylpyrrolidone), 2-sec-butylphenol (SBP), 4-n-pentylphenol (NPP), 4-n-hexylphenol (NHP), THF (tetrahydrofuran), MTHF (methyl-tetrahydrofuran) and DEGDME (di-ethyleneglycol dimethylether).

Next, in step (f) the biphasic system which is formed in step (e) is heated to a temperature within the range of 120-220° C. and is maintained at this temperature range for a time sufficient to form furfural. This will result in a biphasic system comprising furfural. Because of the heating, furfural is produced. The heating time may range from several minutes to several hours. Production of furfural can be monitored by drawing samples and analysing by e.g. HPLC. Thereby, the skilled person can easily monitor the formation of furfural and can decide when to progress to step (g). Step (f) is preferably carried out in two or more continuous stirred-tank reactor (CSTR) reactors which are placed in series. In a CSTR reactor once steady state is reached the concentration of components in the reactor does not change anymore: reactants are withdrawn and substrate is added such that their concentrations remain the same in the reactor. Heating of the hydrolysed biomass in a biphasic system may advantageously prevent any unwanted breakdown of the formed furfural. It may also result in less fouling in subsequent steps of the process. The organic solvent which is added to the first aqueous fraction in step (e) may be pre-heated, preferably to a temperature of at least the temperature which is maintained in step (f) prior to adding said solvent to the first aqueous fraction. This may advantageously shorten the process time. The organic solvent may be preheated to a temperature of between at least 10° C., preferably at least 20° C. above the temperature of step (f).

In step (g) the biphasic system comprising furfural obtained in step (f) is cooled. Cooling is important to prevent breakdown of the formed furfural. Cooling may also be beneficial in a subsequent liquid/separation step.

Optionally, in step (h) the cooled biphasic system obtained in step (g) is subjected to a solid/liquid separation step, recovering the biphasic system. This step also results in a solid fraction. A solid/liquid separation may be advantageous in that any humins, char, and/or tar that may have been formed in step (f), which may otherwise negatively interfere with the separation of the organic phase from the aqueous phase, or later separation steps, are removed. The humins, char and/or tar will predominantly end up in the solid phase and will thus not, or to a lesser extent, affect the subsequent organic/aqueous separation step. Formation of tar, char, and/or humins is a well known problem associated with the production of bio-based products such as levulinic acid, 2,5(hydroxymethyl) furfural (HMF), and 5-methoxymethyl furfural (MMF) by acid hydrolysis of carbohydrates. They create a problem in downstream purification and separation. Tar, sometimes also referred to as "char", is a rather generic term for organic material which is insoluble in water, which is dark in colour and which tends to become viscous and very dark to almost black when concentrated. Tar can be formed during heating of organic material, for example by pyrolysis, but is also formed when carbohydrates are subjected to acid hydrolysis, particularly when done at high temperatures. The presence of tar is undesired for a number of reasons. Firstly, its dark colour makes the product unattractive from the perspective of the user or customer. Secondly, the tar may negatively affect the performance of the bio-based product in the application. For this reason tar is preferably removed before further steps. Humins may also be produced by acid hydrolysis of carbohydrates. Yang and Sen (Chem. Sus. Chem. 2010, vol. 3, 597-603) report the formation of humins during production of fuels from carbohydrates such as fructose. They speculate that the humins are formed by acid-catalyzed dehydration. According to U.S. Pat. No. 7,896,944 the molecular weight of humins ranges from 2.5 to 300 kDa.

Next, in step (i) the cooled biphasic system obtained in step (g), or the recovered biphasic system obtained in step (h), is subjected to a separation step. This results in an organic phase comprising at least part of the furfural and in an aqueous phase comprising at least part of the C6 sugars and optionally further comprising furfural.

Optionally, in step (j) furfural from the organic phase can be recovered, for example by distillation. This will result in recovered furfural and in a recovered organic phase. The recovered organic phase is free of, or at least reduced in furfural, and can advantageously be used again, for example to extract any remaining furfural which is left in the aqueous phase.

In step (k), the recovered organic phase obtained in step can optionally be used to extract furfural from the aqueous phase obtained in step (i) by adding the recovered organic phase to the aqueous phase. Adding the recovered organic phase to the aqueous phase obtained in step (i) will result in a biphasic system, which can be separated to yield an aqueous phase and an organic phase, in other words, step (i) can be repeated using the biphasic system obtained in step (k). Step (k) may be done in countercurrent fashion.

In step (l) water, and optionally an acid, is added to the first solid fraction obtained in step (c) to form a suspension. Suitable acids include inorganic acids such hydrochloric acid, sulphuric acid, nitric acid, and phosphoric acid.

Next, in step (m) the suspension obtained in step (l) is subjected to a temperature of between 140 and 220° C. to form levulinic acid. This normally requires heating of the suspension. Alternatively, prior to adding the water to the solid fraction in step (l), the water may be pre-heated to a temperature of at least the temperature of step (m). The water may be preheated to a temperature of between at least 10° C., preferably at least 20° C. above the temperature of step (m).

In step (n) the suspension comprising levulinic acid, which is obtained in step (m), is subjected to solid/liquid separation to yield a second aqueous fraction comprising levulinic acid and a solid fraction (the first solid fraction being the solid fraction which is obtained in step (c).

Optionally, in step (o) the levulinic acid is recovered from the second aqueous fraction which is obtained in step (n), for example by distillation or crystallization.

The organic solvent in step (e) may comprise at least part of the recovered organic phase obtained in step (j). For example, at least 10% w/w, or preferably at least 20% w/w, more preferably at least 30% w/w, 40% w/w, 50% w/w, more preferably at least 60% w/w, 70% w/w, even more preferably at least 80% w/w, 90% of the organic solvent in step (e) comprises the recovered organic phase obtained in step (j). Ideally, all of the organic solvent in step (e) is the recovered organic phase obtained in step (j)

Using the recovered organic phase obtained in step (j), which is partially, largely, or even completely free of furfural, advantageously reduces the amount of solvent required in the process. It may allow for a continuous process, which is economical and environmentally friendly. It also allows for energy conservation.

The water which is added in step (l) may comprise at least part of the aqueous phase obtained in step (i). For example, at least 10% w/w, or preferably at least 20% w/w, more preferably at least 30% w/w, 40% w/w, 50% w/w, more preferably at least 60% w/w, 70% w/w, even more preferably at least 80% w/w, 90% of the water which is added in step (l) comprises the aqueous phase obtained in step (i). Ideally, all of the water which is added in step (l) is the aqueous phase obtained in step (i). This advantageously allows for the simultaneous production of both levulinic acid and furfural from the same biomass whilst using the water which is a by-product form the furfural production to suspend the solids of the hydrolysate, which can then be heated to produce levulinic acid. This may reduce the amount of water and/or energy needed in the process.

The heating of the biphasic system in step (f), the pre-heating of the organic solvent which is added to the first aqueous fraction, heating of the suspension in step (m), and/or the pre-heating of the water which is added to the first solid fraction may be done through a heat exchange system with the cooling of the biphasic system in step (g). This may reduce the energy consumption considerably.

The invention claimed is:

1. A process for producing furfural and levulinic acid from lignocellulose-comprising biomass, said process comprising:
   (a) adding water and optionally an acid to said biomass to form a slurried biomass;
   (b) subjecting said slurried biomass to hydrolysis to form a hydrolysate comprising C5 and C6 sugars and further comprising (insoluble) cellulose and lignin;
   (c) subjecting said hydrolysate comprising said C5 and C6 sugars and said (insoluble) cellulose and lignin to solid/liquid separation to yield a first aqueous fraction comprising at least part of said C5 and C6 sugars and a first solid fraction comprising at least part of said cellulose and lignin;
   (d) optionally concentrating said first aqueous fraction;
   (e) adding an organic solvent to the optionally concentrated first aqueous fraction to form a biphasic system;
   (f) heating said biphasic system to a temperature within the range of from 120 to 220° C. and maintaining said biphasic system at that temperature range for a time sufficient to form furfural;
   (g) cooling the biphasic system comprising furfural obtained in step (f);
   (h) optionally subjecting the cooled biphasic system obtained in step (g) to solid/liquid separation and recovering the biphasic system;
   (i) subjecting the cooled biphasic system obtained in step (g) or the recovered biphasic system obtained in step (h) to a separation step to yield an organic phase comprising at least part of said furfural and an aqueous phase comprising at least part of said C6 sugars and optionally further comprising furfural;
   (j) optionally recovering furfural from said organic phase;
   (k) optionally using the recovered organic phase obtained in step (j) to extract furfural from the aqueous phase obtained in step (i) by adding said recovered organic phase to said aqueous phase and repeating step (i) and optionally step (j);
   (l) adding water and optionally an acid to the first solid fraction obtained in step (c) to form a suspension;
   (m) subjecting the suspension obtained in step (l) to a temperature of between 140 and 220° C. to form levulinic acid;
   (n) subjecting the suspension comprising levulinic acid obtained in step (m) to solid/liquid separation to yield a second aqueous fraction comprising levulinic acid and a solid fraction; and
   (o) optionally recovering said levulinic acid from the second aqueous fraction.

2. The process according to claim 1, wherein the hydrolysis in step (b) comprises carrying out at a temperature from 140 to 180° C. and at a pH of less than 5.

3. The process according to claim 1, wherein the concentrating in step (d) is completed by evaporation.

4. The process according to claim 1, wherein the organic solvent in step (e) is pre-heated to a temperature of at least the temperature which is maintained in step (f) prior to adding said solvent to the first aqueous fraction.

5. The process according to claim 1, wherein step (f) comprises carrying out in at least two CSTR reactors which are placed in series.

6. The process according to claim 1, wherein step (k) is completed in countercurrent fashion.

7. The process according to claim 1, wherein the organic solvent in step (e) comprises at least part of the recovered organic phase obtained in step (j).

8. The process according to claim 1, wherein the water added to the first solid fraction in step (l) comprises at least part of the aqueous phase obtained in step (i).

9. The process according to claim 8, wherein, prior to adding the water to the first solid fraction, said water is pre-heated to a temperature of at least the temperature of step (m).

10. The process according to claim 1, wherein the heating of the biphasic system in step (f), the pre-heating of the organic solvent which is added to the first aqueous fraction, heating of the suspension in step (m), and/or the pre-heating of the water which is added to the first solid fraction may be completed through a heat exchange system with the cooling of the biphasic system in step (g).

* * * * *